United States Patent
Herbst et al.

(10) Patent No.: US 11,364,011 B2
(45) Date of Patent: Jun. 21, 2022

(54) ULTRASOUND CONTRAST AGENT DECORRELATION-BASED SIGNAL SEPARATION

(71) Applicant: University of Virginia Patent Foundation, Charlottesville, VA (US)

(72) Inventors: Elizabeth Bronwyn Herbst, Charlottesville, VA (US); John A. Hossack, Charlottesville, VA (US); Shiying Wang, Charlottesville, VA (US); F. William Mauldin, Jr., Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 805 days.

(21) Appl. No.: 15/668,404

(22) Filed: Aug. 3, 2017

(65) Prior Publication Data

US 2018/0035979 A1    Feb. 8, 2018

Related U.S. Application Data

(60) Provisional application No. 62/370,958, filed on Aug. 4, 2016.

(51) Int. Cl.
*A61B 8/08* (2006.01)
*A61K 49/22* (2006.01)
(Continued)

(52) U.S. Cl.
CPC .............. *A61B 8/481* (2013.01); *A61B 8/085* (2013.01); *A61K 49/221* (2013.01);
(Continued)

(58) Field of Classification Search
CPC .... A61K 49/221; A61K 49/223; A61B 8/481; A61B 8/085; A61B 8/14; A61B 8/4483; A61B 8/461; A61B 8/5207
See application file for complete search history.

(56) References Cited

U.S. PATENT DOCUMENTS 6,322,505 B1 *  11/2001  Hossack ................. A61B 8/00
                                                600/437
6,364,835 B1 *   4/2002  Hossack ............. G01S 7/52034
                                                600/443
(Continued)

FOREIGN PATENT DOCUMENTS

WO          8002365       11/1980
WO          9942138        8/1999
(Continued)

OTHER PUBLICATIONS

Herbst, Elizabeth B., "The Use of Acoustic Radiation Force Decorrelation-Weighted Pulse Inversion for Enhanced Ultrasound Contrast Imaging", Investigative Radiology, vol. 52, No. 2, (Feb. 2017), 95-102.
(Continued)

*Primary Examiner* — Bo Joseph Peng
(74) *Attorney, Agent, or Firm* — Schwegman Lundberg & Woessner, P.A.

(57) ABSTRACT

An apparatus can be used to generate acoustic imaging pulse sequences and receive corresponding echoes elicited by the acoustic imaging pulse sequences. An acoustic radiation force (ARF) pulse sequence can be generated to agitate a contrast medium in a tissue region between the acoustic imaging pulse sequences. A decorrelation between images corresponding to the received echoes can be determined. A weighting map can be applied to an image to weight a region of the image corresponding to a spatial location of the contrast medium using the determined decorrelation. In an example, the receiving of corresponding echoes elicited by the acoustic imaging pulse sequences can include receiving acoustic energy having a range of frequencies offset from a fundamental frequency associated with the acoustic imaging pulse sequences. An acoustic imaging pulse sequence can
(Continued)

include a pulse having an inverted amplitude envelope with respect to another pulse included in the sequence.

18 Claims, 8 Drawing Sheets

(51) Int. Cl.
    *A61B 8/14*           (2006.01)
    *A61B 8/00*           (2006.01)

(52) U.S. Cl.
    CPC .............. *A61K 49/223* (2013.01); *A61B 8/14* (2013.01); *A61B 8/4483* (2013.01); *A61B 8/461* (2013.01); *A61B 8/5207* (2013.01)

(56) References Cited

U.S. PATENT DOCUMENTS

| | | | |
|---|---|---|---|
| 6,436,041 | B1 | 8/2002 | Phillips et al. |
| 8,093,782 | B1 | 1/2012 | Hossack |
| 9,002,080 | B2 | 4/2015 | Mauldin, Jr. et al. |
| 2005/0124895 | A1* | 6/2005 | Jensen .................. A61B 8/481 600/453 |
| 2005/0154303 | A1 | 7/2005 | Walker et al. |
| 2006/0052697 | A1 | 3/2006 | Hossack et al. |
| 2006/0100516 | A1 | 5/2006 | Hossack et al. |
| 2007/0016022 | A1 | 1/2007 | Blalock et al. |
| 2007/0016044 | A1 | 1/2007 | Blalock et al. |
| 2009/0048519 | A1 | 2/2009 | Hossack et al. |
| 2009/0304246 | A1 | 12/2009 | Walker et al. |
| 2010/0063399 | A1 | 3/2010 | Walker et al. |
| 2010/0168578 | A1 | 7/2010 | Garson, Jr. et al. |
| 2010/0268086 | A1 | 10/2010 | Walker et al. |
| 2010/0331686 | A1 | 12/2010 | Hossack et al. |
| 2011/0137175 | A1 | 6/2011 | Hossack et al. |
| 2011/0137588 | A1 | 6/2011 | Walker et al. |
| 2012/0029356 | A1 | 2/2012 | Hossack et al. |
| 2012/0053460 | A1 | 3/2012 | Blalock et al. |
| 2012/0209116 | A1 | 8/2012 | Hossack et al. |
| 2012/0244564 | A1 | 9/2012 | Walker et al. |
| 2012/0296213 | A1 | 11/2012 | Mauldin, Jr. et al. |
| 2013/0094729 | A1* | 4/2013 | Mauldin, Jr ......... G06K 9/6247 382/128 |
| 2013/0345565 | A1* | 12/2013 | Fan .................... G01S 15/8952 600/442 |
| 2014/0046186 | A1 | 2/2014 | Mauldin, Jr. et al. |
| 2014/0142468 | A1 | 5/2014 | Hossack et al. |
| 2015/0011884 | A1 | 1/2015 | Walker et al. |
| 2015/0025387 | A1 | 1/2015 | Hossack et al. |
| 2015/0133788 | A1 | 5/2015 | Mauldin, Jr. et al. |
| 2015/0150534 | A1* | 6/2015 | Mauldin, Jr ........... A61B 8/481 600/458 |
| 2015/0272601 | A1 | 10/2015 | Dixon et al. |
| 2016/0206867 | A1 | 7/2016 | Hossack et al. |
| 2017/0000458 | A1 | 1/2017 | Blalock et al. |

FOREIGN PATENT DOCUMENTS

| | | |
|---|---|---|
| WO | 03075769 | 9/2003 |
| WO | 2004064619 | 8/2004 |
| WO | 2004064620 | 8/2004 |
| WO | 2004065978 | 8/2004 |
| WO | 2006042067 | 4/2006 |
| WO | 2008154632 | 12/2008 |
| WO | 2009055720 | 4/2009 |
| WO | 2010021709 | 2/2010 |
| WO | 2011011539 | 1/2011 |
| WO | 2011035162 | 3/2011 |
| WO | 2011094585 | 8/2011 |
| WO | 2012148985 | 11/2012 |
| WO | 2013188625 | 12/2013 |
| WO | 2016040008 | 3/2016 |
| WO | 2016094434 | 6/2016 |

OTHER PUBLICATIONS

Shen, Che-Chou, "Pulse Inversion Techniques in Ultrasonic Nonlinear Imaging", J Med Ultrasound, vol. 13, No. 1, (2005), 3-17.

\* cited by examiner

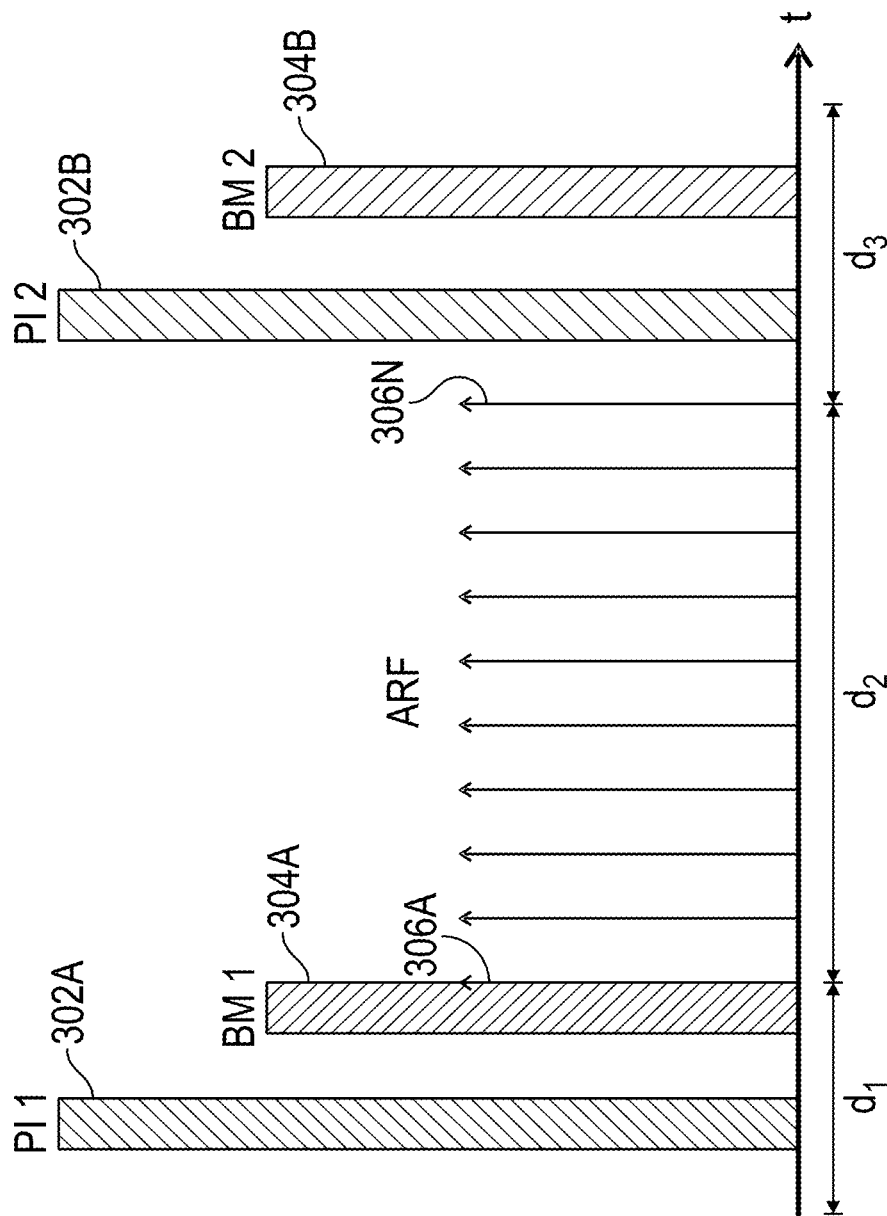

ULTRASOUND CONTRAST AGENT DECORRELATION-BASED SIGNAL SEPARATION

CLAIM OF PRIORITY

This patent application claims the benefit of priority of Mauldin, et al., U.S. Provisional Patent Application Ser. No. 62/370,958, titled "System and Method for Ultrasound Contrast Agent Decorrelation-Based Signal Separation," filed on Aug. 4, 2016, the entirety of which is hereby incorporated by reference herein.

STATEMENT REGARDING FEDERALLY SPONSORED RESEARCH OR DEVELOPMENT

This invention was made with government support under Grant No. HL111077, awarded by the National Institutes of Health. The government has certain rights in the invention.

FIELD OF THE DISCLOSURE

This document pertains generally, but not by way of limitation, to ultrasound imaging, and more particularly to apparatus and techniques for contrast enhancement.

BACKGROUND

Acoustic imaging techniques such as using ultrasonic energy are used in a wide range of different environments including medical and industrial applications. In particular, ultrasound imaging can be useful to assist in diagnosis and screening for cancer. While ultrasound imaging techniques may suffer from various drawbacks, ultrasound imaging does provide the advantage of avoiding exposure of the imaging subject to ionizing radiation. In one approach, the use of ultrasound imaging for cancer diagnosis and screening can be enhanced with the use of molecularly-targeted microbubbles.

OVERVIEW

Acoustic imaging transmission sequences such as pulse inversion (PI) and "contrast pulse sequences" (CPS) can be used to enhance differentiation between a signal corresponding to a contrast agent (e.g., a microbubble signal) and other imaging information. Such pulse sequences can be used to suppress echoes at a fundamental frequency of the transmission pulses, and can be referred generally as "nonlinear" acoustic imaging techniques. The present inventors have recognized, among other drawbacks, that use of such PI or CPS pulse sequences, without more, generally fails to suppress highly echogenic tissue interfaces. This failure can result in one or more of false-positive detection and potential misdiagnosis.

The present inventors have developed an imaging technique that can include use of two or more imaging pulse sequences, and that can optionally include an acoustic radiation force (ARF) pulse sequence, to provide superior detection of a contrast agent. Agitation or other motion of the contrast agent can occur because of such imaging pulse sequences, or between such sequences in response to an ARF pulse sequence. In an example, a decorrelation-based weighting approach can be used to separate motion associated with the contrast medium from static features such as tissue.

As an illustrative example, a combination of acoustic imaging pulse sequences, such as pulse inversion (PI) sequences, can be used along with generation of an ARF pulse sequence. A combination of PI imaging pulse sequences combined with ARF delivery and decorrelation-based weighting can be referred to as ADW-PI. The use of PI sequences is illustrative, and the techniques described herein can include use of other imaging sequences wherein echoes of a fundamental frequency of imaging transmission pulses are suppressed or detection otherwise occurs at a frequency offset from such a fundamental frequency.

Generally, the apparatus and techniques described herein can include applying two or more imaging pulse sequences, and optionally applying acoustic radiation force (ARF) during an imaging sequence to induce adherent microbubble movement, such as while tissue remains static. Alternatively, or in addition, inter-frame registration can be performed to align static features or specified landmarks between frames. The resulting image data is then remapped based on inter-frame signal correlation, suppressing nonlinear tissue signal while maintaining signal from adherent microbubbles. Generally, a combination of a specified pulse transmission sequence, and a decorrelation-based signal separation applied to two or more imaging frames, can be used to separate the signal associated with the contrast agent (e.g., microbubbles) from other imaging information such as echogenic tissue echoes or noise. Use of ARF during the sequence (e.g., between acquisition of imaging frames) can enhance detect of the contrast medium because such a medium will exhibit higher decorrelation than static tissue, for example.

An embodiment, can include, or can optionally be combined with the subject matter of one or any combination of other embodiments herein to include, subject matter (such as an apparatus, a method, a means for performing acts, or a machine readable medium including instructions that, when performed by the machine, that can cause the machine to perform acts), such as can include generating acoustic pulse sequences and receiving corresponding echoes elicited by the acoustic pulse sequences, determining decorrelation between images corresponding to the received echoes, the received echoes corresponding at least in part to a contrast medium in a tissue medium insonified by the acoustic pulse sequences, the contrast medium agitated by the insonation, applying a weighting map to an image to weight at least a region of the image corresponding to a spatial location of the contrast medium using the determined decorrelation. The receiving of corresponding echoes elicited by the acoustic imaging pulse sequences can include receiving acoustic energy having a range of frequencies offset from a fundamental frequency associated with the acoustic imaging pulse sequences.

An embodiment, can include, or can optionally be combined with the subject matter of one or any combination of other embodiments herein to include, subject matter (such as an apparatus, a method, a means for performing acts, or a machine readable medium including instructions that, when performed by the machine, that can cause the machine to perform acts), such as can include an ultrasonic transducer assembly, an ultrasonic transmitter circuit coupled to the transducer assembly, an ultrasonic receiver circuit coupled to the transducer assembly, a display, a processor circuit coupled to the ultrasonic transmitter circuit and ultrasonic receiver circuit, a memory circuit coupled to the processor circuit, the memory circuit including instructions that, when performed by the processor circuit, cause the processor circuit to control the ultrasonic transmitter circuit and the ultrasonic receive circuit to generate acoustic imaging pulse sequences and receive corresponding echoes elicited by the acoustic imaging pulse sequences, respectively. The instructions can cause the processor circuit to control the ultrasonic transmitter circuit to generate an acoustic radiation force (ARF) pulse sequence to agitate a contrast medium in a tissue region between generation of the acoustic imaging pulse sequences. The instructions can cause the processor circuit to determine decorrelation between images corresponding to the received echoes, apply a weighting map to an image to weight a region of the image corresponding to a spatial location of the contrast medium using the determined decorrelation, and present, via the display, the image; Receiving corresponding echoes elicited by the acoustic imaging pulse sequences can include receiving acoustic energy having a range of frequencies offset from a fundamental frequency associated with the acoustic imaging pulse sequences.

This summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3B illustrates generally another example of a sequence of imaging events and an intervening acoustic radiation force transmission sequence, that can be used to obtain decorrelation information, such as for use in weighting (e.g., emphasis or de-emphasis) of a region of interest containing microbubbles, and such as can include pulse inversion (PI) and B-mode imaging sequences for purposes of comparison.

FIG. 5A shows an illustrative example of an image obtained using a B-mode imaging technique. FIG. 5B shows an illustrative example of a pulse inversion (PI) technique, with arrows indicating echogenic tissue boundaries. FIG. 5C shows an illustrative example of a contrast pulse sequence (CPS) technique, including showing a region of microbubbles but also showing a reflection indicated by the arrow. FIG. 5D illustrates generally an illustrative example of an image obtained using the technique of FIG. 4. FIG. 5E shows an illustrative example of an image obtained using the technique of FIG. 4, but having a decorrelation-based filter specified to pass at least some imaging information corresponding to static tissue (e.g., such as shown an discussed in relation to FIG. 8). FIG. 5F shows an illustrative example of an image obtained using the technique of FIG. 4, but without the presence of microbubbles (e.g., pre-injection).

DETAILED DESCRIPTION

Figure 1:
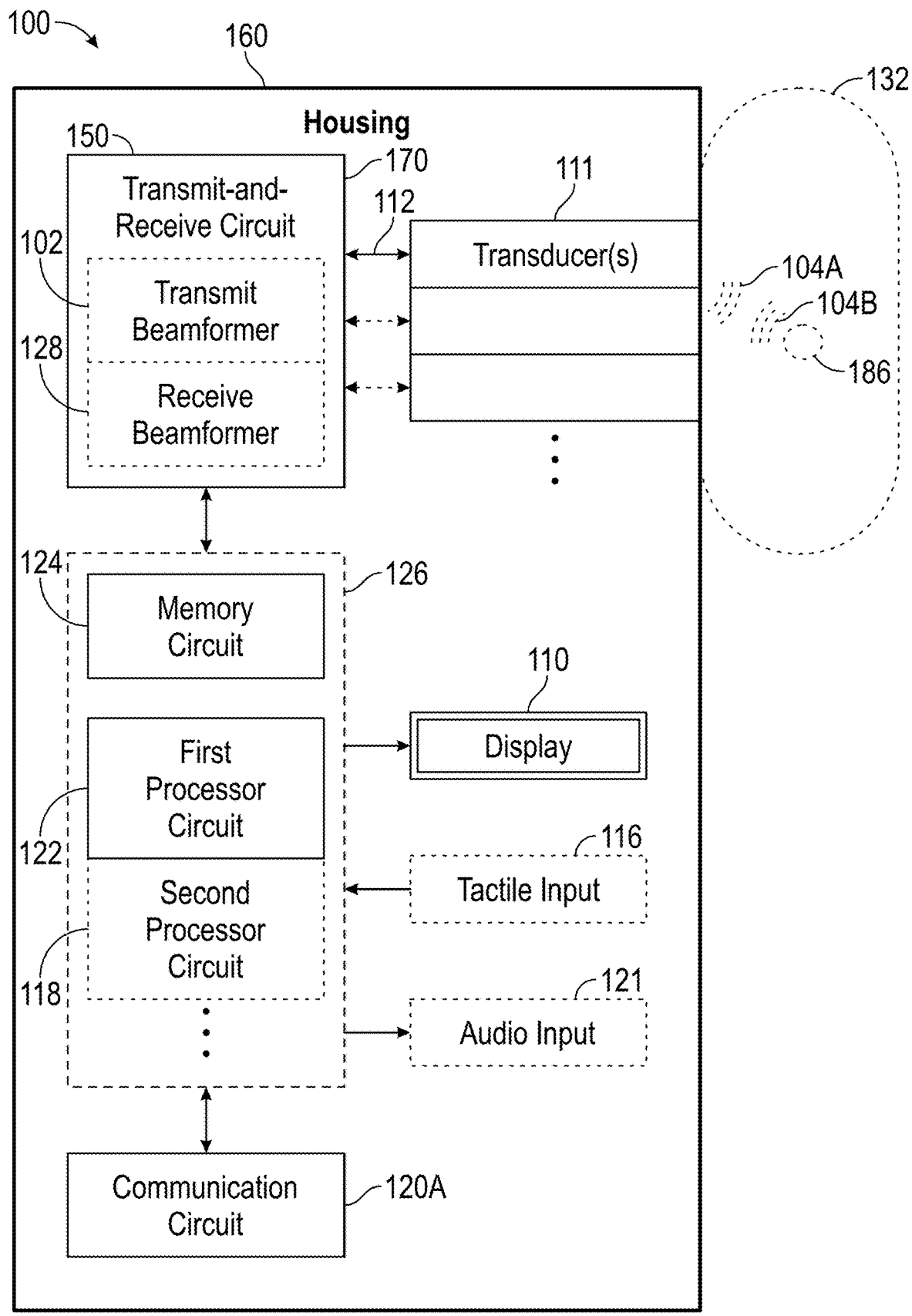
FIG. 1 illustrates generally an example of portions of a system that can include an ultrasonic imaging system, and portions of an environment in which the system can be used.

FIG. 1 illustrates generally an example of portions of a system 100 that can include an ultrasonic imaging system, and portions of an environment in which the system 100 can be used. Such a system 100 can be used to perform one or more techniques described herein, such as using acoustic radiation force in combination with a transmitted acoustic imaging pulse sequence.

In an example, the system 100 can include a first processor circuit 122, a memory circuit 124, a display 110, one or more transducers 111, an analog front-end (e.g., a transmit-and-receive circuit 170) coupled to an array of transducers 111, such as via a bus 112, one or more analog-to-digital (A/D) converters, and digital logic. The transmit-and-receive circuit 150 can include one or more of a transmit beamformer 102, a receive beamformer 128, or other elements. In an illustrative example, the transmit-and-receive circuit 170 can include a transmitter circuit configured to provide one or more imaging sequences such as a pulse inversion (PI) sequence, a contrast pulse sequence (CPS), an amplitude-modulated (AM) sequence, or one or more other sequences, such as an acoustic radiation force (ARF) sequence. Alternatively, or in addition, a separate transmitter circuit can be used to generate an ARF sequence, such as where one or more of an amplitude (e.g., a peak negative pressure), or other characteristics of the pulse sequence differ from the sequence used for an imaging transmission pulse sequence.

One or more of the memory circuit 124, the first processor circuit 122, or one or more additional processor circuits such as a second processor circuit 118 can be included in a computer system 126. Such as computer system 126 can include a hand-held or tablet computer, a desktop computer, a laptop computer, a computer server, or a combination of one or more general purpose or special purpose computers, such as configured to obtain ultrasonic echo information from a transducer block, such as via a wired or wireless communication link.

In an example, a region of interest 132 can include one or more actual targets such as a first target 186. The region of interest 132 can be excited (e.g., insonified, etc.) such as using energy provided by the transducer array 111, such as under the control of the first processor circuit 122. For example, a transmitted ultrasonic energy 104A can propagate through the region of interest 132, and a portion of the transmitted energy 104A can be scattered or reflected by one or more targets, such as the first target 186, to provide an echo 104B. The transducer array 111 can be configured to receive a portion of the echo 104B. The analog front end circuit 170 can be configured for processing the resulting transduced echo signal, such as conditioning, delaying, filtering, or otherwise processing the received echo 104B. Signal processing can further include converting the received energy from an analog signal representation into a digital representation, such as using one or more of the analog-to-digital converters. Such a digital representation can include real-valued information representative of the received energy, or a complex-valued representation that can include real or imaginary parts.

In an array example, one or more of the bus 112, the A/D converters, or the digital logic can include a respective channels corresponding to respective transducers included in the array of transducers 111. For example, a transducer in the array of transducers 111 can be coupled to a respective portion of the analog front end 170, including a respective analog-to-digital converter, or buffered by a respective digital buffer. In an array example, one or more portions of the analog front end 170, the one or more analog-to-digital converters, or the digital logic can be commonly-shared between two or more transducers, such as to simplify the construction of an ultrasonic transducer assembly 160, such as multiplexed over time (e.g., within a single transmission or across multiple transmissions). In an example, the ultrasonic echo information can be processed, such as to reconstruct an image including a representation showing the target 186 or other imaging information such as adherent microbubbles nearby or within a target 186 region. Such processing need not occur using the same computer system 126 as can be used to control the transducer assembly 160.

One or more techniques such as included in the examples below can be machine-implemented or computer implemented, such as performed by the system 100 corresponding to instructions stored in one or more of the memory circuit 124, or stored or obtained from one or more other locations. In an example, one or more of the memory circuit 124 can include a processor-readable medium, such as comprising instructions that when performed by the first or second processors 122, 118, cause the processors or system 100 to perform one or more of the techniques included in the examples discussed below and in relation to other FIGS. such as FIG. 4 or FIG. 8, as illustrative examples.

In an example, the transducer array 111 can be configured to insonify the region of interest 132 using ultrasonic energy, and the region of interest can include a tissue region (e.g., a blood vessel region, or one or more other locations). In such an illustrative tissue imaging example, the target 186 can represent a tissue region of interest, or a molecular species such as including one or more gas bubbles, or generally, any inhomogeneity or scatterer in the region of interest 132. In such an illustrative tissue imaging example, reflected energy can include an ultrasonic echo 104B that can be digitized and converted to an echo data set provided to the computer system 126. For example, the computer system 126 can then construct a representation such as for presentation as an image using the display 128.

The system 100 of FIG. 1 can be used with the examples discussed below. For example, the system 100 can be used for one or more of ultrasound imaging artifact reduction or ultrasound-based targeted molecular imaging, such as can include use of a decorrelation-based weighting approach in combination with acoustic radiation force pulses and transmission of imaging pulse sequences.

Figure 2:
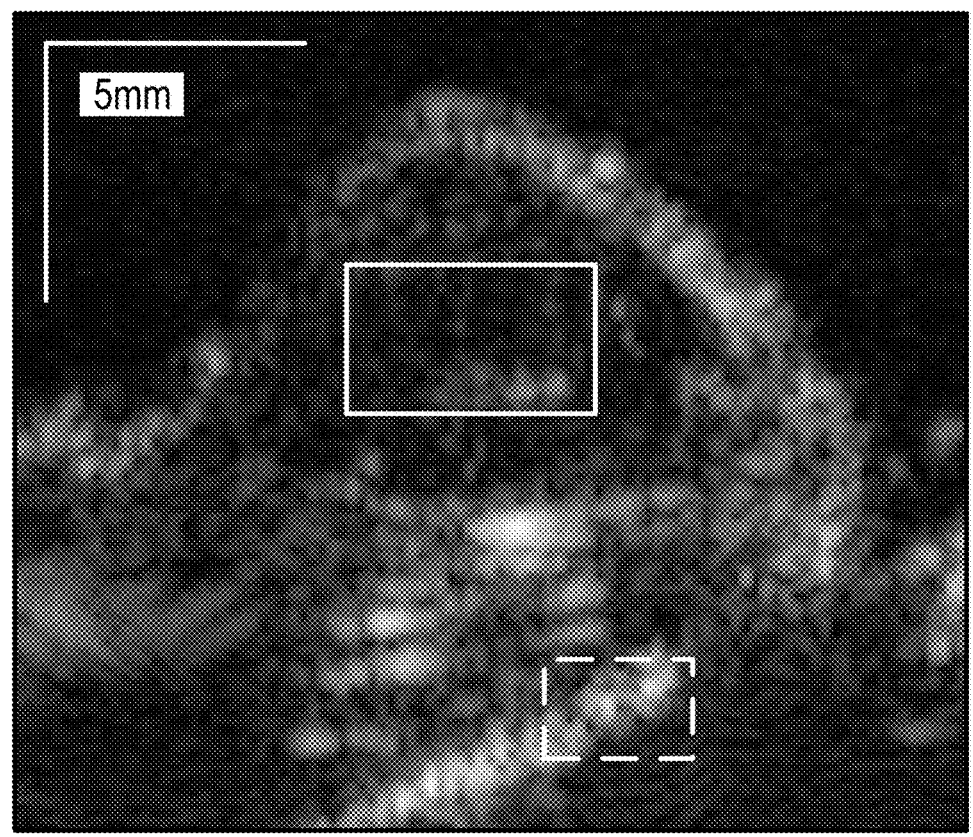
FIG. 2 shows an illustrative example of an image obtained using a pulse inversion (PI) transmit pulse sequence, the imaging including bound microbubbles in a region of interest having a tumor.

FIG. 2 shows an illustrative example of an image obtained using a pulse inversion (PI) transmit pulse sequence, the imaging including bound microbubbles in a region of interest having a tumor. The solid line box shows a region of interest in the interior of a tumor, where bound microbubbles are visible, and the dotted line delineates a region where an unwanted strongly-reflecting tissue signal is clearly visible.

The phrase "microbubbles" can generally refer to lipid-shelled perfluorocarbon gas bubbles that are used as ultrasound contrast agents for medical imaging due to their high echogenicity and biocompatibility. Microbubbles generally exhibit a nonlinear response when insonified at diagnostic ultrasound frequencies. Such a response can be distinguishable from linear acoustic reflections. Linear reflections or echoes generally refer to fundamental, nonharmonic echoes produced by most tissues. Because of the relatively high echogenicity and generation of harmonic signals, non-targeted microbubbles are currently approved for use in medical settings, such as to visualize left ventricular opacification. An ability to identify tumorigenic tissue based on molecular targeting rather than the presence of anatomical features can greatly improve the sensitivity and specificity of diagnostic ultrasound imaging. Various pulse sequences can be used to elicit non-linear reflections, and such techniques can include "contrast pulse sequences" (CPS) or pulse inversion (PI). Such techniques can be used to visualize microbubbles through the extraction of harmonic signals. However, without more, such pulse transmission sequences can be susceptible to misclassifying harmonic signals produced by highly echogenic tissue surfaces such as bone or vascular walls. Accordingly, the present inventors have recognized that a problem exists in isolating a signal generated by tissue-bound microbubbles while suppressing a signal from other tissues.

While the harmonic-to-fundamental reflected energy ratio within tissue may be lower than that of microbubbles, sufficiently echogenic tissue interfaces may generate reflections in both the fundamental and harmonic frequencies strong enough to be clearly visible in most ultrasound imaging systems. Moreover, harmonic signal amplitudes can generally increase nonlinearly as a function of transmit power, which can compound this unwanted reflection effect as transmit pressure increases. The present inventors have recognized that existing contrast pulse sequence techniques exhibit insufficient cancelation of harmonics from highly echogenic tissue interfaces. The present inventors have recognized, among other things, that acoustic radiation force (ARF) pulses can be used to induce motion in adherent microbubbles. In addition, or alternatively, multiple imaging pulse sequences can be used to achieve such induced motion, though such motion may be further enhanced by use of ARF in combination with imaging pulse sequences, rather than imaging pulse sequences alone.

Without being bound by theory, it is believed that the applied ARF (or, for example, a correspondingly powerful imaging pulse sequence) can induce small microbubble displacements, which give rise to a decorrelation effect that can be used to separate a signal corresponding to the microbubbles from tissue reflections and noise. Nondestructive imaging pressures can be used to induce small movements of microbubbles, and separate the movement of microbubbles from static tissue based on the microbubbles' detectable inter-frame signal decorrelation properties, induced by ARF pulses. In this manner, an improved contrast-to-tissue ratio can be realized.

In the illustrative examples described in this document, biotinylated gas-filled microbubbles were produced by a sonication protocol from decafluorobutane gas (F2 Chemicals; Lancashire, United Kingdom) by dispersing gas in a lipid micellar mixture of distearoyl phosphatidylcholine (Avanti Polar Lipids; Alabaster, Ala.), polyethylene glycol stearate (Stepan Kessco, Elwood, Ill.), and biotin-PEG3400-distearoylphosphatidylethanolamine (PEG-DSPE; Shearwater Polymers, Huntsville, Ala.) in normal saline to create microbubbles coated with a lipid monolayer shell. After preparation, microbubbles were sealed in vials under decafluorobutane headspace atmosphere and stored refrigerated. Immediately before antibody coupling, microbubbles were centrifuged for 10 minutes (140 g) in degassed phosphate-buffered saline to eliminate the excess of unincorporated lipid from the solution and counted using a Coulter Multisizer 3 (Beckman Coulter, Brea, Calif.).

Biotinylated microbubbles were conjugated to biotinylated antimouse VEGFR2 antibody (clone Avas 12a1; eBioscience, San Diego, Calif.) using streptavidin (Anaspec Inc, Fremont, Calif.) as a linking molecule. Streptavidin was added to the biotinylated microbubble solution at a concentration of 3 micrograms (µg) per 10 million microbubbles and incubated for 15 minutes at room temperature. During incubation, the microbubbles were gently agitated every 2 minutes to ensure mixing. The microbubble solution was washed twice with phosphate-buffered saline to remove excess streptavidin and counted again. The biotinylated anti-VEGFR2 antibody was added to the microbubbles at 1.5 µg per 10 million microbubbles and incubated for 10 minutes. Two more washing operations were performed to remove the excess antibody. Microbubble count and size distribution was acquired before each experiment.

Figure 3A:
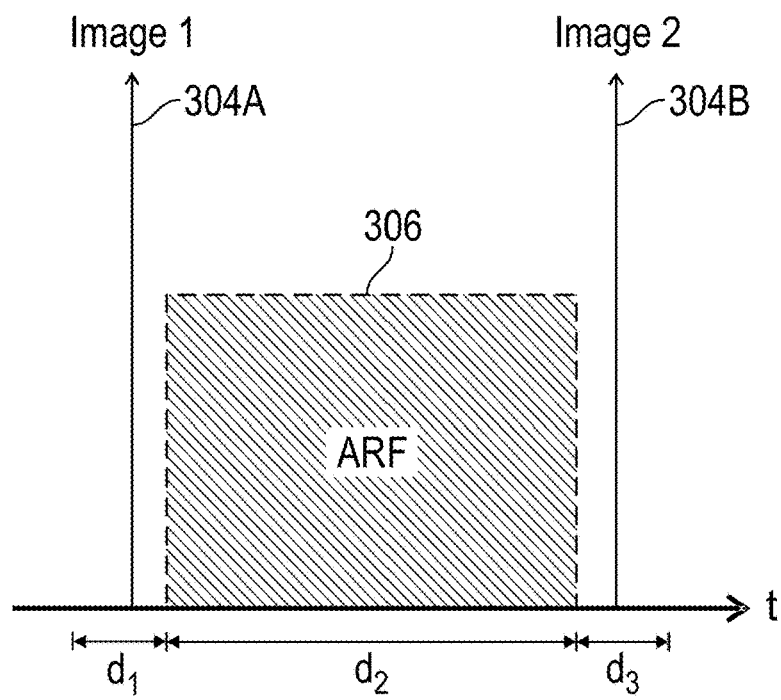
FIG. 3A illustrates generally an example of a sequence of imaging events and an intervening acoustic radiation force transmission sequence, that can be used to obtain decorrelation information, such as for use in weighting (e.g., emphasis or de-emphasis) of a region of interest containing microbubbles.

FIG. 3A illustrates generally an example of a sequence of imaging events 304A, 304B, and optionally, an intervening acoustic radiation force (ARF) transmission sequence 306, that can be used to obtain decorrelation information, such as for use in weighting (e.g., emphasis or de-emphasis) of a region of interest containing microbubbles. During duration $d_1$, an acoustic transmission pulse sequence 304A can be delivered, such as to obtain one or more imaging frames before application of the ARF transmission sequence 306, and a second acoustic transmission pulse sequence 304B can be delivered during duration $d_3$. The acoustic transmission pulse sequences 304A and 304B can include at least one of a pulse inversion (PI) sequence, a contrast pulse sequence (CPS), or an amplitude modulation (AM) sequence. The acoustic transmission pulse sequence can include pulses selected to suppress echoes at the fundamental frequency. Receiving of elicited echoes can include receiving acoustic energy having a range of frequencies offset from a fundamental frequency associated with the first and second acoustic imaging pulse sequences. As an illustration, a pulse inversion (PI) sequence can include a sequence of pulses having normalized amplitudes of {1, −1, 1, . . . }. A contrast pulse sequence (CPS) can include pulses having normalized amplitudes such as having a transmission amplitude {½, −1, ½, . . . } and a corresponding receive weighting. Other pulse sequences, such as an amplitude modulated sequence, can include normalized amplitudes such as {1, ½, ½, 1, −½, −½, . . . } or other variations. The pulse sequence can be generated to suppress first order (e.g., linear) reflections.

During the duration $d_2$, an ARF sequence can be generated. The ARF sequence include bursts or individual pulses delivered in a sequence. The pulses can have a uniform center frequency and amplitude, or the parameters of the pulses can be varied over duration $d_2$. For example, a separation between adjacent ARF pulses or bursts need not be uniform. Generation of the ARF pulse sequence can include use of at least one of a range of frequencies, a burst duration, a count of bursts, an overall burst sequence length, or a focusing scheme that differs from pulse sequences used for the first and second acoustic imaging pulse sequences 304A and 304B. Generally, the ARF pulse sequence includes an amplitude (e.g., a peak negative pressure) that is lower than corresponding amplitudes of the first and second acoustic imaging pulse sequences 304A and 304B. If a focusing scheme is used for imaging, a different scheme can be used for ARF sequences. For example, if focusing is performed on a line-by-basis for the imaging and receive operations, an ARF sequence can include an entirely different scheme, such as a beam or slice approach, having overlapping or non-overlapping regions of insonification for successive ARF pulses.

FIG. 3B illustrates generally another example of a sequence of imaging events and an intervening acoustic radiation force transmission sequence 306A through 306N, that can be used to obtain decorrelation information, such as for use in weighting (e.g., emphasis or de-emphasis) of a region of interest containing microbubbles, and such as can include pulse inversion (PI) and B-mode imaging sequences for purposes of comparison. During duration $d_1$, a PI imaging transmission pulse sequence 302A can be generated, and for purposes of comparison, a b-mode transmission pulse sequence 304A can be generated. During duration $d_2$, an acoustic radiation force (ARF) pulse sequence can be generated including bursts or pulses 306A through 306N. During duration $d_3$, another PI imaging transmission pulse sequence 302B can be generated, and for purposes of comparison, another b-mode transmission pulse sequence 304B can be generated.

For the illustrative examples described herein wherein experimental results were obtained, tumors were imaged using a 128-element L12-5 38 millimeter (mm) linear array transducer (Philips Healthcare, Andover, Mass.). The imaging sequences were programmed on a Verasonics programmable ultrasound scanner (Vantage 256; Verasonics, Redmond, Wash.) and involved a combination of PI and synthetic aperture virtual source element imaging. The 64 central transmit and receive elements were designated as the synthetic aperture, with 22 virtual source elements distributed laterally with foci located 35 mm behind the transducer face.

Each virtual source element transmitted a positive and negative waveform, and the resulting 44 receive signals (1 positive and 1 negative receive for each source element) were summed to create 1 complete PI image, such as corresponding to the first sequence 302A or the second sequence 302B of FIG. 3B. The PI image acquisition was followed by a B-mode image, in which only the positive transmit/receive signals from each virtual source were performed and summed. Pulse inversion imaging was transmitted at a frequency of 5.5 megahertz (MHz), and a bandpass filter was applied to the receive signal, centered at a harmonic (11 MHz). B-mode transmit and receive was performed at a center frequency of 11 MHz, within the passband of the applied filter. In-phase/quadrature (IQ) data were used for all receive signals to preserve variations in both signal amplitude and phase.

Control sequences in which no ARF was applied included 1 PI image and 1 B-mode image, followed by a delay of approximately 3 milliseconds, then a second PI and B-mode image acquisition. This corresponds to the sequence shown in FIG. 3B, but with ARF during duration $d_2$ suppressed. The transducer position was held stationary throughout all B-mode and PI image sequences in a given tumor. In the illustrative examples shown herein, the ARF sequences included ten 15-cycle, 4.4-MHz ARF waveforms were transmitted at a pulse repetition frequency of 11.4 kHz for 875 µs during the 3 milliseconds delay (e.g., during duration $d_2$). For both the control (no ARF) and ARF sequences, a complete sequence of transmit events was repeated at a frame rate of approximately 15 Hz for 5 seconds. Acoustic radiation force transmissions had a measured MI of 0.12 and peak negative pressure of approximately 0.25 MPa. For comparison to a commercially available standard of nonlinear imaging, CPS images of the microbubble-bound tumor were taken using a Siemens Sequoia clinical scanner with a 15L8-5 transducer, at a center frequency of 7 MHz and frame rate of 12 Hz. These images were taken immediately after the ARF, and no-ARF trial data had been collected.

An imaging plane within the tumor was located using a Verasonics programmable scanner, and the transducer was secured in place. The tumor was imaged before microbubble injection. A bolus injection of about $2 \times 10^7$ microbubbles was administered retro-orbitally and allowed to circulate and bind for 15 minutes before imaging. The microbubble-bound tumors were then imaged again using a Verasonics programmable scanner and a Siemens Sequoia commercial scanner.

Figure 4:
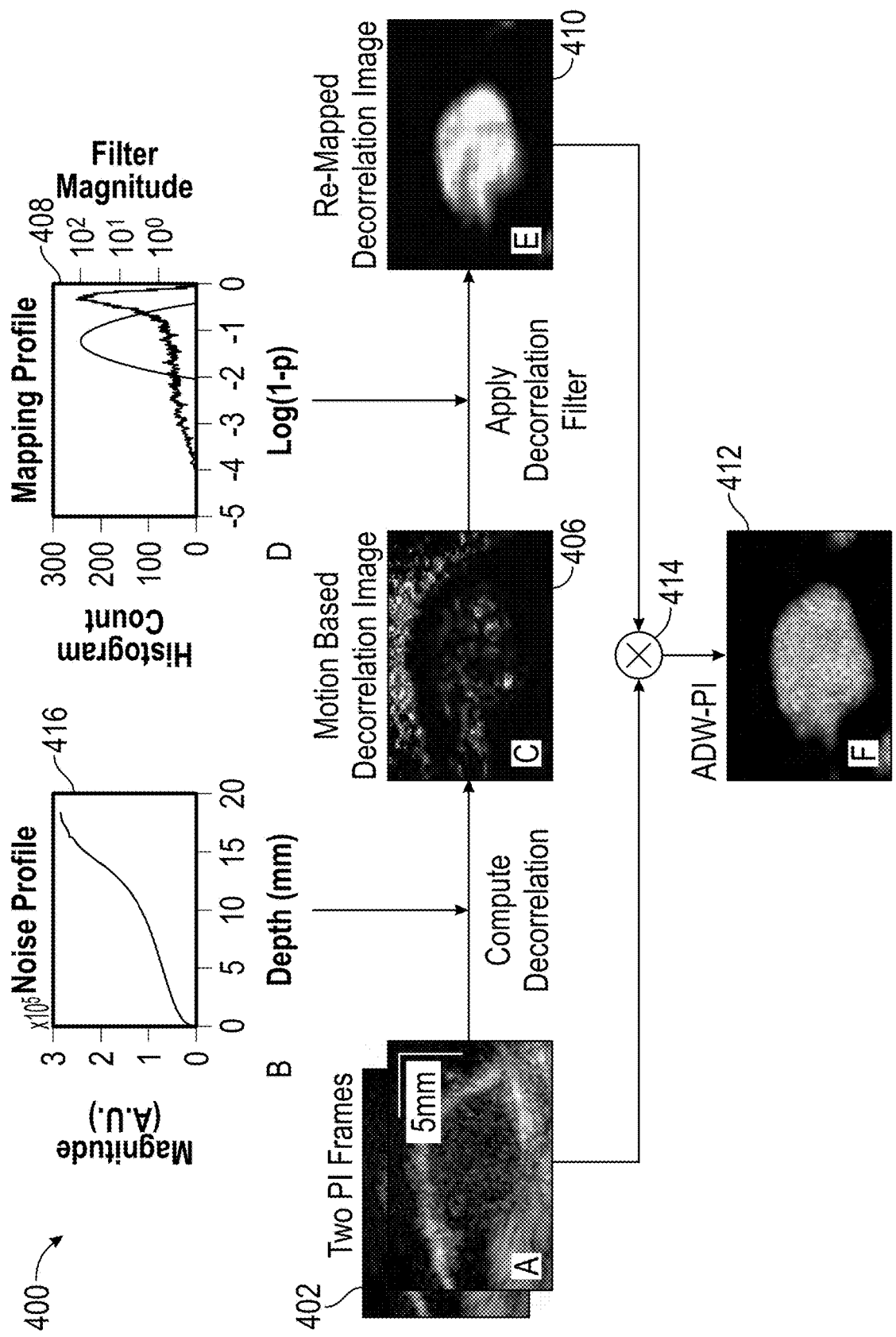
FIG. 4 illustrates generally a technique, such as a method, that can include generating imaging pulse sequences, generating an acoustic radiation force pulse sequence, generating a weighting map using information obtained by decorrelation of obtained imaging information, and applying the weighting map to an image to emphasize a region of the image corresponding to a spatial location of a contrast medium.

FIG. 4 illustrates generally a technique 400, such as a method, that can include at 402 generating imaging pulse sequences to obtain two or more imaging frames. At 402, an acoustic radiation force (ARF) pulse sequence can also be generated, such as to enhance motion of a contrast medium. At 410, a weighting map using information obtained by decorrelation at 406 of obtained imaging information can be generated, and at 414, the weighting map can be applied to an image to weight (e.g., emphasize or de-emphasize) a region of the image corresponding to a spatial location of a contrast medium, such as to produce a resulting weighted representation 412, such as an image for presentation to a user. One or more other similarity metrics can be used, as mentioned elsewhere herein.

In particular, in an example, at 406, pre-ARF and post-ARF images obtained at 402 can be compared to each other for similarity. A similarity metric can be determined using, as illustrative examples, an inter-frame signal correlation, a sum of absolute differences, a normalized one-dimensional (1D) or two-dimensional (2D) cross-correlation, or a normalized singular spectrum area. These similarity measurements can then be used as inputs into a mapping function where high similarity between frames is mapped to low values and low similarity is mapped to high values, such as shown at 408. An output, shown at 410, of the mapping function can be multiplied by the original image at 414, such as to product a final image at 412 of microbubble signal along with an attenuated tissue signal. The technique 400 shown in FIG. 4 can include other operations. For example, a noise profile can be obtained at 416, and a contribution from the noise profile 416 can be removed from an image including the similarity metric values, such as the image shown at 406. In an example, inter-frame registration can be performed such as to align one or more features in the imaging frames acquired at 402 before determining a similarity metric such as decorrelation between the imaging frames.

In the example of FIG. 4, a decorrelation-based weighting filter can be applied to the mapping profile at 408, such as to suppress imaging information corresponding to static or slow-moving features such as tissue. A noise contribution (appearing as a spike in the decorrelation values to the right of the weighting filter) can also be suppressed using the weighting filter. In this manner, low-decorrelation information (e.g., tissue information) and high-decorrelation information (e.g., noise) can be attenuated to provide a resulting re-mapped decorrelated image at 410 that can be used as a map to weight one or more of the imaging frames obtained at 402.

Imaging information obtained by receiving echoes elicited by acoustic pulse transmission sequences at 402 generally includes complex-valued (e.g., "IQ") sample data. In the illustrative example described herein, for each sample in an acquired image, a 3×3 pixel window surrounding a sample of interest was selected for both pre-ARF and post-ARF images. A correlation coefficient between pre-ARF and post-ARF windows was numerically determined using a "corrCoef" function in MATLAB (Mathworks, Natick, Mass.), and signal decorrelation was determined as the complement of signal correlation. This determination, when performed for respective samples in the image, resulted in a decorrelation image as shown at 406, illustratively. Without being bound by theory, a determined signal decorrelation between imaging frames was assumed to arise from two additive sources: motion and electronic noise. To isolate decorrelation arising from motion, techniques can be performed to estimate, and account for, the decorrelation due to electronic noise. To estimate decorrelation from electronic noise, it was generally assumed that signal decorrelation arising from electronic noise could be approximated by the following equation:

$$\rho_{r_1 r_2} = SNR / \sqrt{SNR^2 + 1} \qquad (1)$$

The value, $\rho_{r_1 r_2}$, can represent a signal-to-noise (SNR) based correlation coefficient between two signals. A measurement of noise intensity through depth was acquired by collecting, as an illustrative example, 50 frames of receive data without any transmission signal while applying the same time gain compensation settings as used in other imaging acquisitions. In the absence of an ultrasound transmit pulse sequence, only electronic noise was received by the system. A line of each frame of electronic noise was averaged to obtain an approximation of noise intensity though depth, as shown illustratively in the noise profile at 416. To estimate a combined signal and noise intensity for each ultrasound image, a root-mean-square calculation was performed for samples in the images using a 3×3 pixel window of values from which to determine a root-mean-square value. An estimate of the signal and noise could then be determined for each pixel in each image, and these values were evaluated using EQN. (1) to obtain an estimate of the signal decorrelation component due to electronic noise alone. The noise-based decorrelation image was then subtracted from the original decorrelation image to generate an estimate of signal decorrelation arising from motion, as shown illustratively at 406.

Motion-induced decorrelation images were remapped using a Gaussian-shaped remapping filter centered at the expected decorrelation range exhibited by microbubbles. The Gaussian mapping function parameters for standard deviation and mean were applied uniformly and set by evaluating a specificity to microbubble signal using frames of image data collected from the test subjects during the experimental evaluation. For example, for each mouse used for the experimentally-obtained results described herein, an image was reconstructed using 15 decorrelation images that were spatially median filtered and then compounded. The resulting compounded decorrelation image was multiplied at 414 by an original image to form a resulting representation at 412.

Figure 5A:
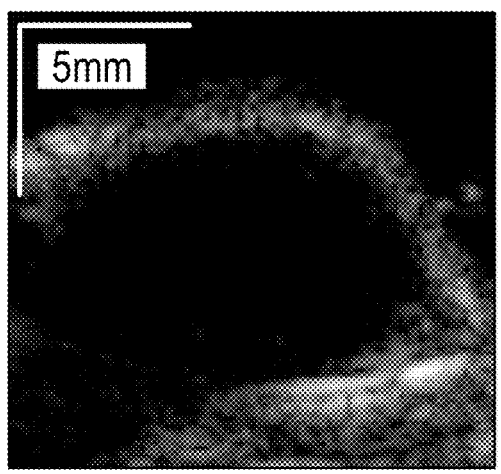
FIGS. 5A through 5F show examples of images obtained using various techniques.
Figure 5B:
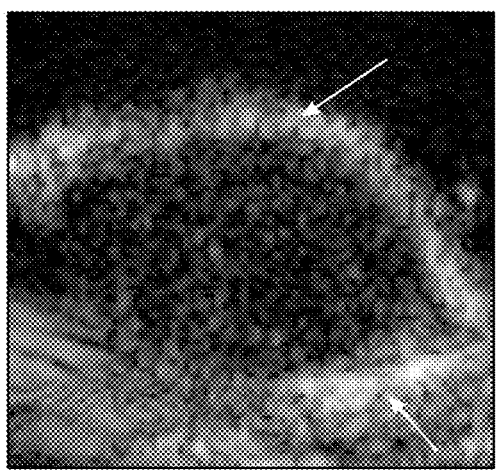
Figure 5C:
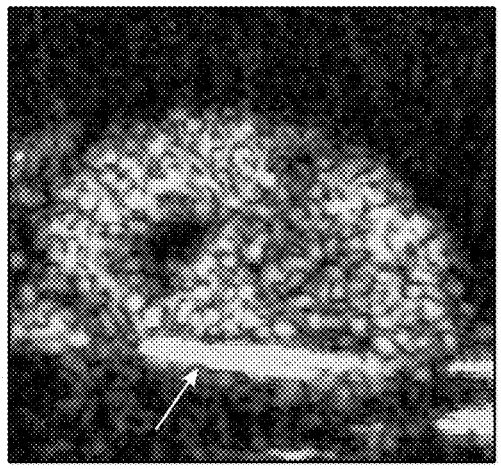
Figure 5D:
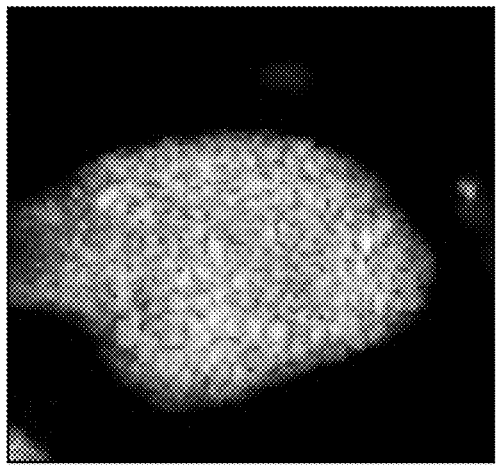
Figure 5E:
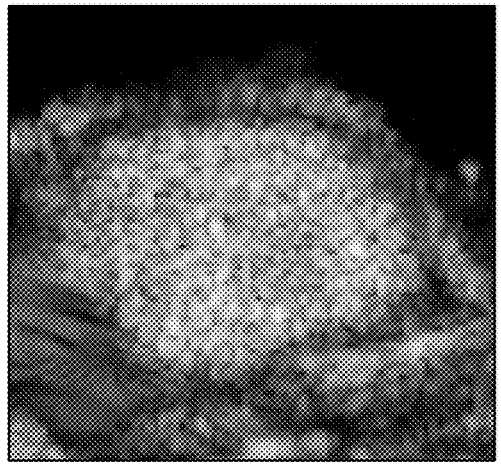
Figure 5F:

FIGS. 5A through 5F show examples of images obtained using various techniques. FIG. 5A shows an illustrative example of an image obtained using a B-mode imaging technique. FIG. 5B shows an illustrative example of a pulse inversion (PI) technique, with arrows indicating echogenic tissue boundaries. FIG. 5C shows an illustrative example of a contrast pulse sequence (CPS) technique, including showing a region of microbubbles but also showing a reflection indicated by the arrow. FIG. 5D illustrates generally an illustrative example of an image obtained using the technique of FIG. 4. FIG. 5E shows an illustrative example of an image obtained using the technique of FIG. 4, but having a decorrelation-based filter specified to pass at least some imaging information corresponding to static tissue (e.g., such as shown an discussed in relation to FIG. 8). FIG. 5F shows an illustrative example of an image obtained using the technique of FIG. 4, but without the presence of microbubbles (e.g., pre-injection).

In the illustrative examples of FIGS. 5A through 5F, each image is displayed at a 50-dB dynamic range. In FIG. 5A, corresponding to a B-mode image, no microbubbles are visible within the tumor interior. In FIG. 5B, corresponding to pulse inversion transmit sequence, microbubble contrast is improved over B-mode, but PI imaging fails to cancel an echogenic tissue signal, such as the bright signal visible at the femur and skin line (as shown by arrows). In FIG. 5C, corresponding to a contrast pulse sequence, microbubbles are visible, but signal from the mouse femur remains prominent (as shown by the arrow). In FIG. 5D, corresponding to ARF decorrelation-weighted PI ($\alpha=0$), suppression of bright tissue signal and preservation of signal from bound microbubbles occurs. In FIGS. 5E and 5F, respectively, ADW-PI imaging ($\alpha=0.75$) is performed showing a post-injection and pre-injection tumor data set.

Figure 6:
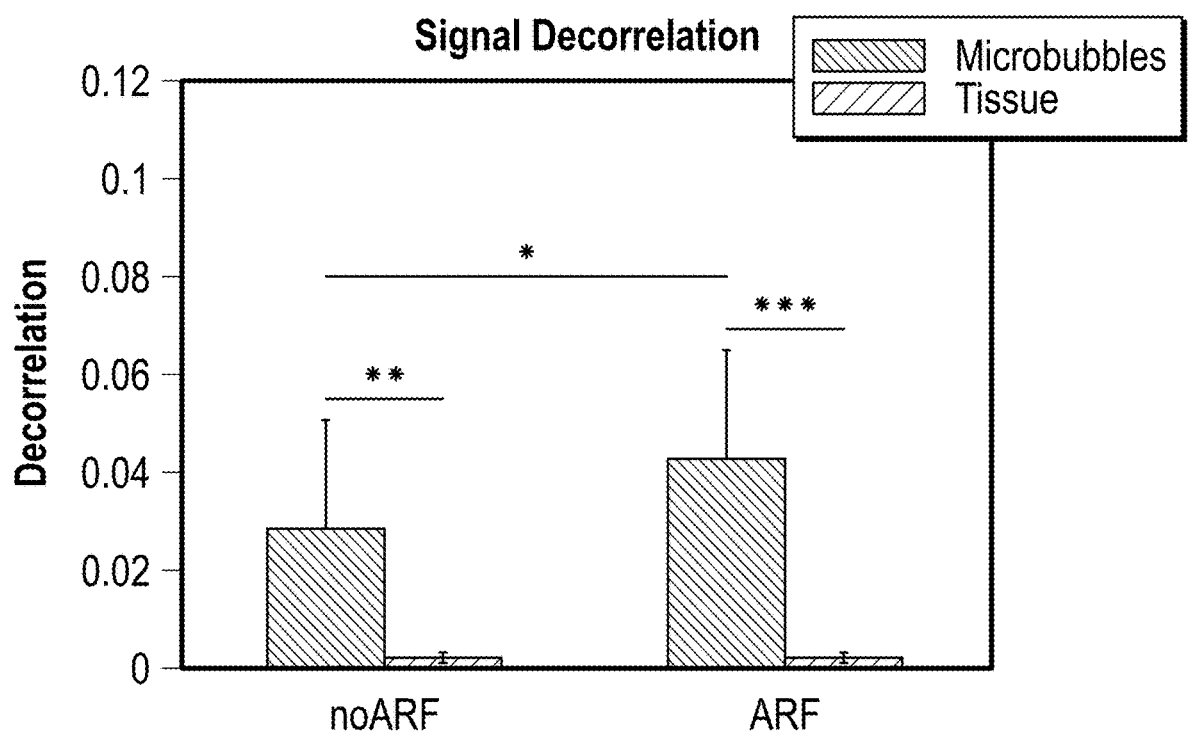
FIG. 6 shows an illustrative example of decorrelation values corresponding to tissue and microbubble regions with the application of acoustic radiation force (ARF) and without ARF (labeled "noARF").

FIG. 6 shows an illustrative example of decorrelation values corresponding to tissue and microbubble regions with the application of acoustic radiation force (ARF) and without ARF (labeled "noARF"). In the illustrative examples described herein, based on experimentally-obtained results, across 9 mice, the mean decorrelation within microbubble ROIs for PI image pairs was 0.028 when ARF was not applied and 0.043 when ARF was applied. Such "noARF" results indicate that decorrelation exists between microbubble contrast regions and static tissue with the application of two or more imaging pulse sequences, and the ARF results indicate that decorrelation (and hence contrast) of the microbubble contrast medium can be further enhanced through application of ARF pulses.

The increased signal decorrelation within microbubble-bound regions allowed for significant differentiation between ARF-insonated microbubble signal and a static tissue signal ($P<0.001$). A one-sided t test performed on the difference between the microbubble signal decorrelations of ARF and no-ARF trials showed that the measured microbubble signal decorrelation for ARF trials was significantly higher than that of no-ARF trials ($P<0.01$). Control measurements of tissue signal decorrelation in both ARF and no-ARF trials also showed that ARF does not increase decorrelation uniformly throughout the entire image. In particular, no statistically significant difference in tissue signal decorrelation was found between ARF and no-ARF conditions, as shown illustratively in FIG. 6.

Figure 7:
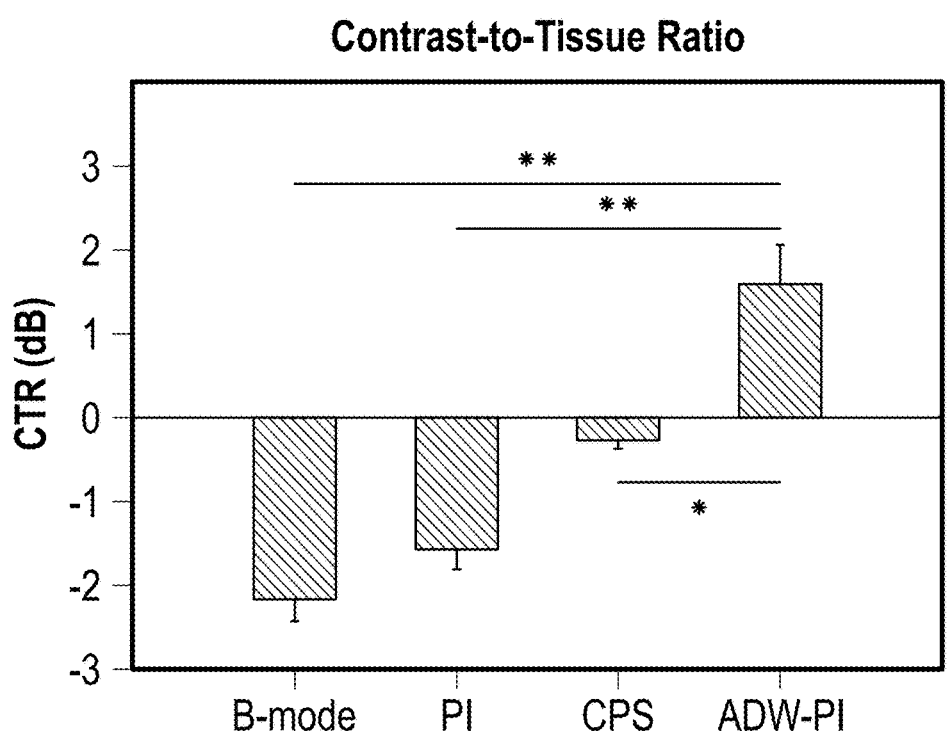
FIG. 7 shows illustrative examples of contrast-to-tissue ratios for various imaging modes including B-mode, pulse inversion (PI) without acoustic radiation force (ARF), contrast pulse sequence (CPS) without acoustic radiation force, and ADW-PI which refers to ARF decorrelation-weighted (ADW) pulsed inversion (PI) imaging.

FIG. 7 shows illustrative examples of contrast-to-tissue ratios (CTRs) for various imaging modes including B-mode, pulse inversion (PI) without acoustic radiation force (ARF), contrast pulse sequence (CPS) without acoustic radiation force, and ADW-PI which refers to ARF decorrelation-weighted (ADW) pulsed inversion (PI) imaging. As shown illustratively in the experimentally-obtained results of FIG. 7, an acoustic radiation force-based decorrelation weighting allowed for effective suppression of echogenic tissue interfaces from nearby bone structures visible in non-ARF B-mode, PI, and CPS images of the same tumor. The contrast-to-tissue ratio (CTR) of ADW-PI was increased by almost 2 dB when compared with corresponding non-ARF CPS images, and at least 3 dB when compared with corresponding B-mode and PI images. As discussed in relation to FIG. 8, below, a decorrelation-based filter or other filter based on a similarity metric can be adjusted to different levels of specified parameter, "$\alpha$," to allow for selective enhancement or suppression of a signal corresponding to static tissue, such as for limited visualization of surrounding tissue structures. Measurements of contrast between post-injection and pre-injection intra-tumor ROIs showed an average signal enhancement of 17.6 dB ($P<0.05$) after injection of microbubbles.

In the illustrative examples described herein, a microbubble signal received from within a tumor exhibited significantly higher inter-frame signal decorrelation than static tissue, with and without the application of ARF ($P<0.005$). It was also found that the application of ARF significantly increased the signal decorrelation of microbubbles ($P<0.01$), without causing significant changes in tissue signal decorrelation.

A comparison of post-microbubble injection ADW-PI signal to pre-microbubble injection control further demonstrated that ADW-PI isolated the microbubble signal rather than the tumor tissue (17.6 dB average contrast improvement; $P<0.05$). There are several sources of microbubble movement that were possible contributors to microbubble signal decorrelation. For example, secondary radiation forces may have resulted in lateral and out-of-beam motion of microbubbles as they deformed or detached from the vessel wall in response to applied ARF.

Secondary radiation forces can manifest as attraction between individual targeted microbubbles in vitro and cause rapid deformation of microbubbles into a prolate shape. These deformations in the microbubble shell could have manifested as axial motion, which can result in a detectable phase shift and resulting signal decorrelation. Another factor may be that as ARF insonation pressure increases, secondary radiation force can overcome molecular binding forces, and allow bound microbubbles to dislodge or cluster.

As an illustrative example, a peak negative pressure for secondary radiation forces to overcome the molecular binding forces of adherent microbubbles was approximately 150 kPa. In the imaging sequences used for experimentally-obtained results described herein, PI, B-mode, and ARF transmissions had peak negative pressures of 286, 115, and 255 kPa, respectively, without accounting for attenuation. As a result, it is possible that some portion of microbubbles detached from the vessel wall even in the absence of ARF pulses.

The addition of ARF pulses in the imaging sequence likely resulted in a higher percentage of bound microbubbles that dislodged over time, and a resulting increase in out-of-beam motion may account for the higher signal decorrelation observed in ARF versus no-ARF trials. The dynamics of blood flow in tumor microvasculature may be another source of bound microbubble movement and signal decorrelation. For example, shear forces from flow are a cause of microbubble signal decorrelation in large blood vessels, as continuous microbubble aggregation and dislodgement creates out-of-beam motion. This motion can lead to significant increases in the adherent microbubble normalized single spectrum area values, which may be monotonic with signal decorrelation. Shear forces are more difficult to characterize in the microvasculature of a tumor, where blood flow is non-Newtonian with lower velocity. A combination of shear and collision forces from red blood cells in the tumor may induce out-of-beam detachment of targeted microbubbles, similar to what has been observed in large vessels.

VEGFR2-targeted microbubbles generally exhibit a high specificity in adherence to a tumor endothelium. A concentration of targeted biomarkers in a tumor is generally correlated with an amount of adherent microbubbles present in the image, and signal enhancement is generally monotonic with microbubble concentration. For the measurements described herein, complex-valued samples were used (including in-phase, or "I" components, and quadrature or "Q" components). This preserves amplitude and phase information in the acquired samples. When the complex-valued echo data were ignored and only the absolute signal intensity was used to determine inter-frame signal decorrelation, no statistically significant difference was found between ARF-insonated microbubbles and no-ARF microbubbles.

These results may indicate that phase information, acquired from the complex component of echo data, assists in revealing an ARF-based enhancement in microbubble signal decorrelation. Changes in signal phase can be correlated with axial motion of microbubbles, assessed through the "slow-time," frame-to-frame dimension, it is possible that the enhancement of decorrelation in ARF-insonated trials is due to axial movement of adherent microbubbles.

Generally, axial movement of acoustic targets can lead to signal basis functions with highly overlapping frequency components. Such frequency overlap can lead to periodicity in real echo data while complex echo data were not affected. Fully processed images from a commercially-available scanner in CPS contrast mode were used to compare the CTR between CPS and ADW-PI. CPS data were displayed on a 0-to-50 dB dynamic range, and determination of CPS CTR assumed linear gamma mapping in grayscale. However, it is likely that non-linear steps were used to form the final CPS image from the commercially-available scanner. An assumption of image linearity may lead to minor inaccuracy in CTR measurements, determinations of CTR were still viable for an approximate comparison between contrast imaging modes.

Figure 8:
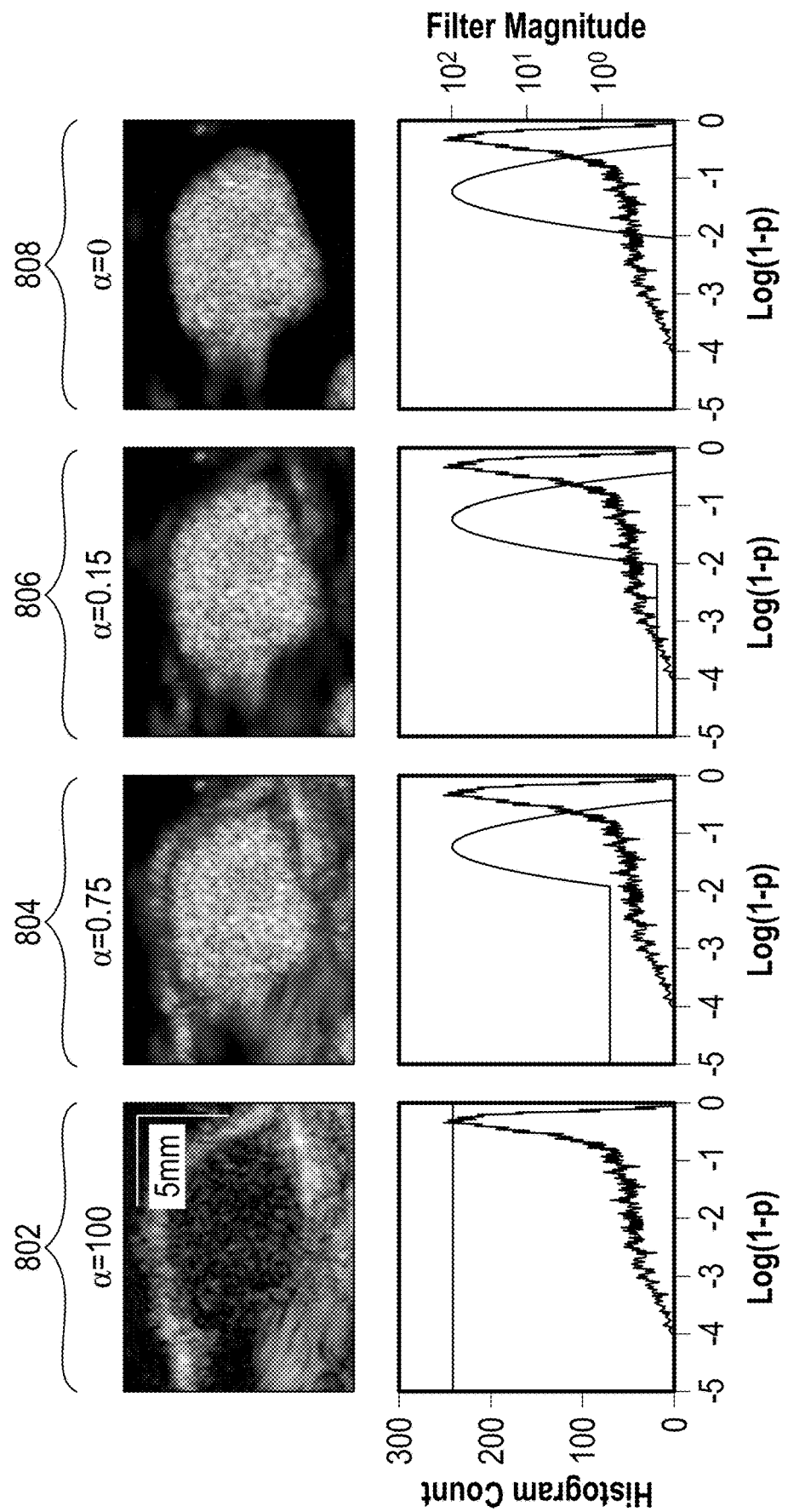
FIG. 8 shows various illustrative examples of images obtained using the technique of FIG. 4, but having a decorrelation-based filter including a parameter, "α," specified to pass at least some imaging information corresponding to static tissue.

FIG. 8 shows various illustrative examples of images obtained using the technique of FIG. 4, but having a decorrelation-based filter including a parameter, "$\alpha$," specified to pass at least some imaging information corresponding to static tissue. A value of $\alpha$ can determine a level at which the signal components exhibiting low-decorrelation, such as corresponding to static tissue, are displayed. When $\alpha$ is set to zero, a signal associated with the contrast medium (e.g., microbubbles) can be isolated from all other anatomical features.

When displaying ADW-PI images for the illustrative examples including experimentally-obtained data herein such as in FIG. 8, a parameter $\alpha$ was used to set the intensity of decorrelation values lower than those encompassed by a Gaussian-shaped remapping filter. These low-decorrelation signals were assumed to be static tissue. High values of $\alpha$ allowed for more tissue signal to be displayed in ADW-PI images, whereas lower values of $\alpha$ caused tissue signal suppression. In this manner, a decorrelation-based filter including a specified profile as a function of decorrelation value can include a portion having a weighting to selectively pass or suppress imaging information corresponding to tissue that is static between acoustic imaging pulse sequences (e.g., such as tissue that is static between acquired imaging frames). In FIG. 8, at 808, $\alpha=0$. At 806, $\alpha=0.15$; at 804, $\alpha=0.75$; and as a control, at 802, $\alpha=100$. The $\alpha$ values shown in FIG. 8 represent the level of the line extending to the left of the Gaussian-shaped remapping filter. The region to the right of the Gaussian filters remains rejected, and generally corresponds to noise having decorrelation values beyond the values of interest corresponding to the contrast medium signal.

Figure 9:
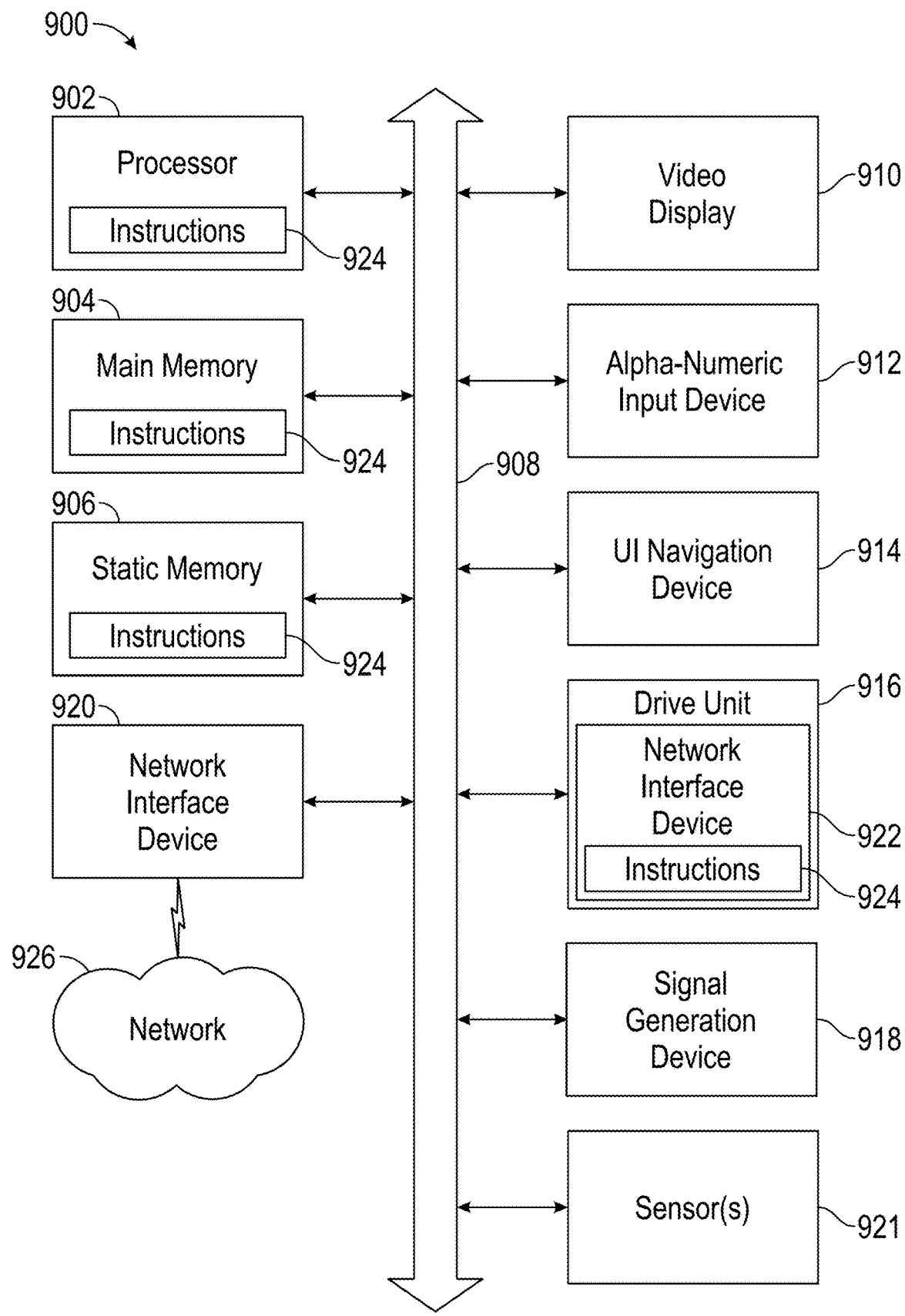
FIG. 9 illustrates generally a block diagram of an example that can include a machine upon which one or more embodiments (e.g., discussed methodologies described herein) can be implemented (e.g., run), such as where the machine is included as a portion of the system shown in FIG. 1 or where the system in FIG. 1 is communicatively coupled to the machine of FIG. 9.

FIG. 9 illustrates generally a block diagram of an example that can include a machine 900 upon which one or more embodiments (e.g., discussed methodologies described herein) can be implemented (e.g., run), such as where the machine is included as a portion of the system 100 shown in FIG. 1 or where the system 100 in FIG. 1 is communicatively coupled to the machine 900 of FIG. 9. Examples of the machine 900 can include logic, one or more components, or circuits. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field-programmable gate array (FPGA) or an application-specific integrated circuit (ASIC). In an example, a circuit can include programmable logic (e.g., circuitry, as encompassed within a general-purpose processor or other programmable processor) that can be temporarily configured (e.g., by software) to perform the certain operations. It will be appreciated that apparatus and techniques described herein can be implemented in a circuit mechanically (e.g., in dedicated and permanently configured circuitry), or in temporarily configured circuitry (e.g., configured by software).

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where a multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which at least one of the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of techniques described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Generally, the techniques described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment, or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Examples of various embodiments (e.g., apparatus, systems, or methods) can be implemented in digital electronic circuitry, in computer hardware, in firmware, in software, or in any combination thereof. Examples of various embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Certain functionality can be implemented in permanently configured hardware (e.g., an ASIC), or in temporarily configured hardware (e.g., a combination of software and a programmable processor), for example.

In an example, the machine 900 can operate as a stand-alone device or the machine 900 can be connected (e.g., networked) to other machines. In a networked deployment, the machine 900 can operate in the capacity of either a server or a client machine in server-client network environments. In an example, the machine 900 can act as a peer machine in peer-to-peer (or other distributed) network environments. The machine 900 can be a personal computer (PC), a tablet PC, a set-top box (STB), a Personal Digital Assistant (PDA), a hand-held application-specific assembly, a mobile telephone, a web appliance, a network router, switch or bridge, or any machine capable of executing instructions (sequential or otherwise) specifying actions to be taken (e.g., performed) by the machine 900. Further, while only a single machine 900 is illustrated, the term "machine" shall also be taken to include any collection of machines that individually or jointly execute a set (or multiple sets) of instructions to perform any one or more of the methodologies discussed herein.

In an example, the machine (e.g., computer system) 900 can include a processor 902 (e.g., a central processing unit (CPU), a graphics processing unit (GPU) or both), a main memory 904 and a static memory 906, some or all of which can communicate with each other via a bus 908 or other link. The machine 900 can further include a display unit 910, an alphanumeric input device 912 (e.g., a keyboard), and a user interface (UI) navigation device 911 (e.g., a mouse, a touch-screen, or one or more soft-keys, as illustrative examples). In an example, the display unit 910, input device 912 and UI navigation device 914 can be a touch screen display. The machine 900 can additionally include a storage device (e.g., drive unit) 916, a signal generation device 918 (e.g., a speaker), a network interface device 920, and one or more sensors 921, such as a global positioning system (GPS) sensor, compass, accelerometer, or other sensor.

The storage device 916 can include a machine readable medium 922 on which is stored one or more sets of data structures or instructions 924 (e.g., software) embodying or utilized by any one or more of the methodologies or functions described herein. The instructions 924 can also reside, completely or at least partially, within the main memory 904, within static memory 906, or within the processor 902 during execution thereof by the machine 900. In an example, one or any combination of the main memory 904, the static memory 906, or the storage device 916 can comprise a machine readable medium or machine readable media.

While the machine readable medium 922 is illustrated as a single medium, the term "machine readable medium" can include a single medium or multiple media (e.g., a centralized or distributed database, and/or associated caches and servers) that configured to store the one or more instructions 924. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 924 can further be transmitted or received over a communications network 926 using a transmission medium via the network interface device 920 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone Service (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Various Notes

Each of the non-limiting aspects described herein can stand on its own, or can be combined in various permutations or combinations with one or more of the other aspects or other subject matter described in this document.

The above detailed description includes references to the accompanying drawings, which form a part of the detailed description. The drawings show, by way of illustration, specific embodiments in which the invention can be practiced. These embodiments are also referred to generally as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:
1. A method, comprising:
  generating a first acoustic imaging pulse sequence to insonify a tissue region;

receiving first echoes elicited by the first acoustic imaging pulse sequence from the tissue region;

generating a non-imaging acoustic radiation force (ARF) pulse sequence to displace a contrast medium in the tissue region;

generating a second acoustic imaging pulse sequence to insonify the tissue region, the tissue medium displaced by insonation using the non-imaging acoustic radiation force (ARF) pulse sequence applied between the generation of the first and second acoustic imaging pulse sequences;

receiving second echoes elicited by the second acoustic imaging pulse sequence from the tissue region;

generating a weighting map by evaluation of decorrelation between images generated from the received first echoes and the received second echoes, the decorrelation enhanced by the non-imaging acoustic radiation force (ARF) pulse sequence; and applying the weighting map to an image to weight at least a region of the image, the region corresponding to a spatial location of the contrast medium to emphasize or de-emphasize the spatial location of the contrast medium in the image.

2. The method of claim 1, wherein at least one of the first or second acoustic imaging pulse sequences is selected to suppress echoes at a fundamental frequency; and wherein the receiving the first and second echoes includes receiving acoustic energy having a range of frequencies offset from the fundamental frequency associated with the first and second acoustic imaging pulse sequences.

3. The method of claim 1, wherein the first and second acoustic imaging pulse sequences include at least one of a pulse inversion (PI) sequence, a contrast pulse sequence (CPS), or an amplitude modulation (AM) sequence.

4. The method of claim 1, wherein the contrast medium comprises microbubbles.

5. The method of claim 4, wherein the microbubbles are adherent to a region of interest for performing contrast imaging of the region of interest.

6. The method of claim 1, wherein the receiving the first and second echoes includes receiving acoustic energy in a range of frequencies including a subharmonic or an integer multiple of fundamental frequency.

7. The method of claim 1, wherein applying the weighting map to the image comprises applying the weighting map to at least one of a first image constructed using the received first echoes or a second image constructed using the received second echoes.

8. The method of claim 1, wherein the generating the weighting map includes applying a decorrelation-based filter to select and weigh a specified range of decorrelation values.

9. The method of claim 8, wherein the decorrelation-based filter includes a Gaussian profile as a function of decorrelation value.

10. The method of claim 8, wherein the decorrelation-based filter includes a specified profile as a function of decorrelation value, the profile including a portion having a weighting to selectively pass or suppress imaging information using the value.

11. The method of claim 1, wherein the generating the weighting map comprising generating the weighting map using imaging information obtained by decorrelation between images generated from the received first echoes and the received second echoes comprises:

performing a receive operation without a corresponding transmit operation to obtain a noise profile; and modifying imaging information corresponding to at least one of the received first echoes or the received second echoes using the noise profile to provide suppression of noise corresponding to the noise profile.

12. The method of claim 1, wherein generating the ARF pulse sequence comprises using at least one of a range of frequencies, a burst duration, a count of bursts, an overall burst sequence length, or a focusing scheme that differs from pulse sequences used for the first and second acoustic imaging pulse sequences.

13. The method of claim 1, wherein generating the ARF pulse sequence comprises using an amplitude that is lower than corresponding amplitudes of the first and second acoustic imaging pulse sequences.

14. The method of claim 1, wherein generating the ARF pulse sequence includes varying at least one parameter of the respective ARF pulses over a duration of the ARF pulse sequence or over a duration of respective ARF pulse sequences.

15. A method, comprising:

generating acoustic pulse sequences to insonify a tissue region and receiving corresponding echoes elicited by the acoustic pulse sequences from the tissue region, the acoustic pulse sequences comprising at least two acoustic imaging pulse sequences, the at least two acoustic imaging pulse sequences separated by an intervening non-imaging acoustic radiation force (ARF) pulse sequence;

determining decorrelation between images generated from the received echoes, the received echoes corresponding at least in part to a contrast medium in a tissue medium insonified by the acoustic pulse sequences, the contrast medium displaced using the non-imaging acoustic radiation force (ARF) pulse sequence and the decorrelation enhanced by the non-imaging acoustic radiation force (ARF) pulse sequence; and applying a weighting map to an image to weight at least a region of the image, the region corresponding to a spatial location of the contrast medium using the determined decorrelation to emphasize or de-emphasize the spatial location of the contrast medium in the image;

wherein the receiving corresponding echoes elicited by the acoustic imaging pulse sequences includes receiving acoustic energy having a range of frequencies offset from a fundamental frequency associated with the acoustic imaging pulse sequences.

16. The method of claim 15, wherein the at least two acoustic imaging pulses sequences include at least one of a pulse inversion (PI) sequence, a contrast pulse sequence (CPS), or an amplitude modulation (AM) sequence.

17. The method of claim 15, wherein the contrast medium comprises microbubbles.

18. An apparatus, comprising:

an ultrasonic transducer assembly;

an ultrasonic transmitter circuit coupled to the transducer assembly;

an ultrasonic receiver circuit coupled to the transducer assembly;

a display;

a processor circuit coupled to the ultrasonic transmitter circuit and ultrasonic receiver circuit;

a memory circuit coupled to the processor circuit, the memory circuit including instructions that, when performed by the processor circuit, cause the processor circuit to control the ultrasonic transmitter circuit and the ultrasonic receive circuit to generate acoustic imaging pulse sequences and receive corresponding echoes elicited by the acoustic imaging pulse sequences from a tissue region, respectively;

wherein the instructions cause the processor circuit to control the ultrasonic transmitter circuit to generate a non-imaging acoustic radiation force (ARF) pulse sequence to displace a contrast medium in the tissue region between generation of the acoustic imaging pulse sequences; and wherein the instructions cause the processor circuit to:

determine decorrelation between images corresponding to the received echoes, the decorrelation enhanced by the non-imaging acoustic radiation force (ARF) pulse sequence; and apply a weighting map to an image to weight a region of the image, the region corresponding to a spatial location of the contrast medium using the determined decorrelation to emphasize or de-emphasize the spatial location of the contrast medium in the image; and present, via the display, the image;

wherein the receiving corresponding echoes elicited by the acoustic imaging pulse sequences includes receiving acoustic energy having a range of frequencies offset from a fundamental frequency associated with the acoustic imaging pulse sequences.

\* \* \* \* \*